(12) United States Patent
Fukuzaki et al.

(10) Patent No.: US 11,179,486 B2
(45) Date of Patent: Nov. 23, 2021

(54) WET WIPER

(71) Applicants: Mie University, Tsu (JP); Kuraray Kuraflex Co., Ltd., Okayama (JP)

(72) Inventors: Satoshi Fukuzaki, Tsu (JP); Yasurou Araida, Osaka (JP); Masako Yokomizo, Okayama (JP)

(73) Assignees: Mie University, Tsu (JP); Kuraray Kuraflex Co., Ltd., Okayama (JP)

( * ) Notice: Subject to any disclaimer, the term of this patent is extended or adjusted under 35 U.S.C. 154(b) by 0 days.

(21) Appl. No.: 16/334,236

(22) PCT Filed: Sep. 21, 2017

(86) PCT No.: PCT/JP2017/034126
§ 371 (c)(1),
(2) Date: Mar. 18, 2019

(87) PCT Pub. No.: WO2018/056365
PCT Pub. Date: Mar. 29, 2018

(65) Prior Publication Data
US 2019/0255203 A1 Aug. 22, 2019

(30) Foreign Application Priority Data

Sep. 23, 2016 (JP) .............................. JP2016-185727

(51) Int. Cl.
*A61L 2/18* (2006.01)
*D06M 11/30* (2006.01)
(Continued)

(52) U.S. Cl.
CPC .................. *A61L 2/18* (2013.01); *A47K 7/00* (2013.01); *A47L 13/17* (2013.01); *A61L 2/16* (2013.01);
(Continued)

(58) Field of Classification Search
None
See application file for complete search history.

(56) References Cited

U.S. PATENT DOCUMENTS 4,998,984 A * 3/1991 McClendon ........... A01N 25/34
15/104.93
7,066,916 B2 * 6/2006 Keaty, Jr. ............ A61M 35/006
604/290
(Continued)

FOREIGN PATENT DOCUMENTS

CN 1283718 A 2/2001
CN 1414902 A 4/2003
(Continued)

OTHER PUBLICATIONS

Shirata et al. JP2010184043A—translated document (Year: 2010).*
(Continued)

*Primary Examiner* — Jelitza M Perez
(74) *Attorney, Agent, or Firm* — Oblon, McClelland, Maier & Neustadt, L.L.P.

(57) ABSTRACT

It is an object to provide a novel wet wiper in which a sterilization effect and a wiping/cleaning effect are maintained even when the wet wiper is stored for a long period of time. A wet wiper is provided which includes: a fabric; and a chlorine-based treatment agent included in the fabric, wherein the chlorine-based treatment agent includes at least one of chlorous acid ($HClO_2$), chlorite ion ($ClO_2^-$), and chlorine dioxide ($ClO_2$) as an effective chlorine component.

20 Claims, 8 Drawing Sheets

(51) Int. Cl.
*D06M 16/00* (2006.01)
*A47K 7/00* (2006.01)
*A61L 2/16* (2006.01)
*A47L 13/17* (2006.01)
*D06M 101/06* (2006.01)

(52) U.S. Cl.
CPC ............ *D06M 11/30* (2013.01); *D06M 16/00* (2013.01); *A61L 2202/17* (2013.01); *D06M 2101/06* (2013.01)

(56) References Cited

U.S. PATENT DOCUMENTS

| | | | | | |
|---|---|---|---|---|---|
| 2011/0020473 | A1* | 1/2011 | Ogata | ..................... | A61P 31/12 424/665 |
| 2014/0066872 | A1* | 3/2014 | Baer | ..................... | A61F 13/538 604/367 |

FOREIGN PATENT DOCUMENTS

| | | | |
|---|---|---|---|
| CN | 101011595 A | | 8/2007 |
| CN | 101658397 A | | 3/2010 |
| CN | 101745137 A | | 6/2010 |
| CN | 101812803 A | | 8/2010 |
| CN | 102233141 A | | 11/2011 |
| CN | 102596754 A | | 7/2012 |
| JP | 54-102495 | | 2/1981 |
| JP | 2001-336056 A | | 12/2001 |
| JP | 2004-097462 A | | 4/2004 |
| JP | 2004-105431 A | | 4/2004 |
| JP | 2007-29264 A | | 2/2007 |
| JP | 2008-156329 A | | 7/2008 |
| JP | 2008156329 A | * | 7/2008 |
| JP | 2008-213194 A | | 9/2008 |
| JP | 3157042 U | | 1/2010 |
| JP | 2010-162343 A | | 7/2010 |
| JP | 2010162343 A | * | 7/2010 |
| JP | 2010-184043 A | | 8/2010 |
| JP | 2010184043 A | * | 8/2010 |
| JP | 2012-249921 A | | 12/2012 |
| JP | 2012249921 A | * | 12/2012 |
| JP | 2015-110544 A | | 6/2015 |
| JP | 2016-22273 A | | 2/2016 |
| WO | WO-2014188312 A2 | * | 11/2014 ............ A01N 59/26 |
| WO | WO 2015/191811 A1 | | 12/2015 |
| WO | WO2016/052527 A1 | | 4/2016 |

OTHER PUBLICATIONS

Sekiguchi, N. JP2008156329A—translated document (Year: 2008).*
Shirata et al. JP2010184043—translated document (Year: 2014).*
Horiguchi et al. Antimicrobial Activity and Stability of Weakly Acidified Chlorous Acid Water. Biocontrol Science. vol. 20, No. 1, p. 43-51 https://www.jstage.jst.go.jp/article/bio/20/1/20_43/_pdf (Year: 2015).*
Sekiguchi et al. JP2008156326A—translated document (Year: 2008).*
Horiuchi et al. Antimicrobial Activity and Stability of Weakly Acidified Chlorous Acid Water. Biocontrol Science. vol. 20, No. 1, pp. 43-51. https://www.jstage.jst.go.jp/article/bio/20/1/20_43/_pdf (Year: 2015).*
Tojo, et al. JP2010162343A—translated document (Year: 2010).*
Sekiguchi et al. JP2008156329A—translated document (Year: 2008).*
Oshima et al. JP2012249921A—translated document (Year: 2012).*
International Search Report dated Dec. 19, 2017 in PCT/JP2017/034126 filed Sep. 21, 2017.
Partial Supplementary European Search Report dated Apr. 15, 2020, in Patent Application No. 17853133.1, 11 pages.
Office Action dated Sep. 14, 2020, in Korean Patent Application No. 10-2019-7011083, with English translation, (14 pages).
Combined Chinese Office Action and Search Report dated May 27, 2020 in Patent Application No. 201780058473.9 (with English translation), 21 pages.
Shunzhen Ding, et al. "Practical Nursing Management of Clean Surgical Suites" Beijing Union Medical College Press, Jun. 30, 2012, 5 pages.
Yaozong Geng. "Modern Aqueous Coating Processes, Formulations and Application" China Petrochemical Press, Mar. 31, 2003, 5 pages.
Office Action dated Sep. 20, 2021, in European Patent Application No. 17853133.1, filed Sep. 21, 2017.

* cited by examiner

FIG.1
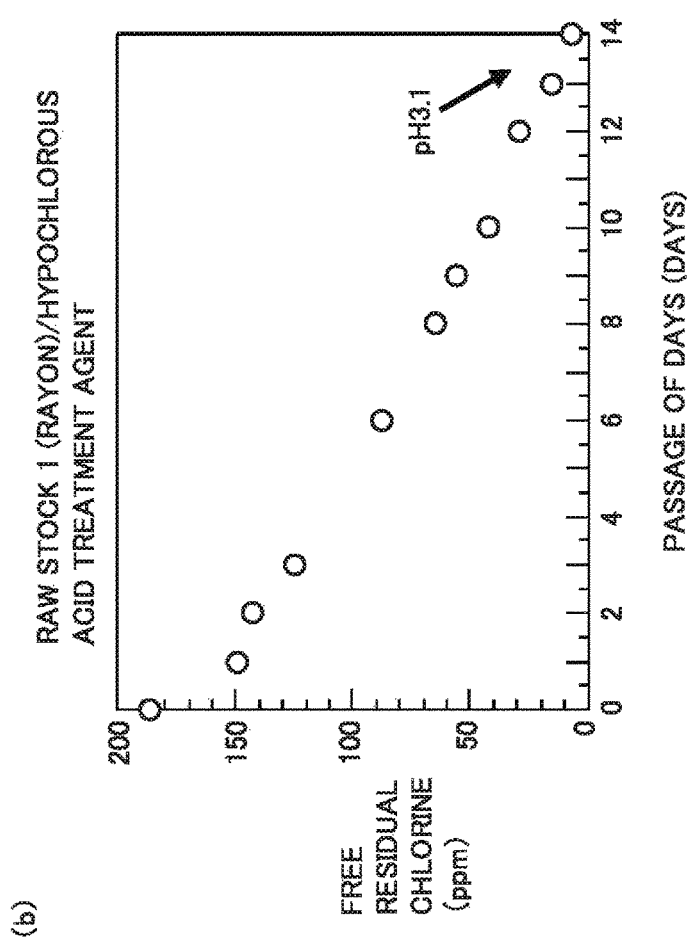
(a)
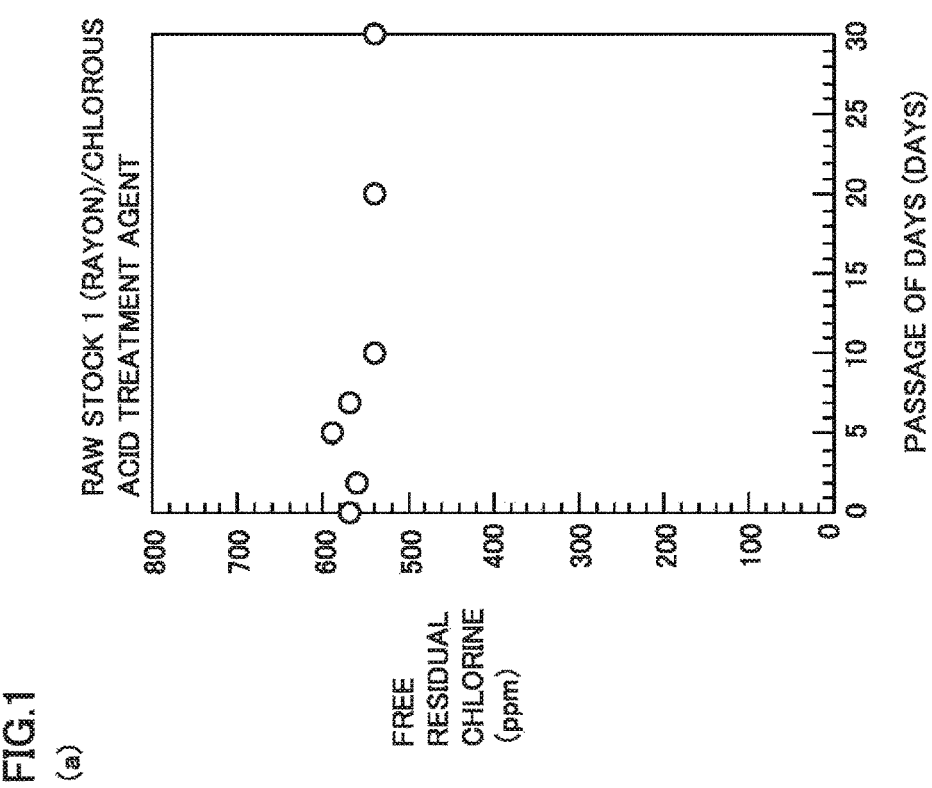
(b)

FIG.2
(a)
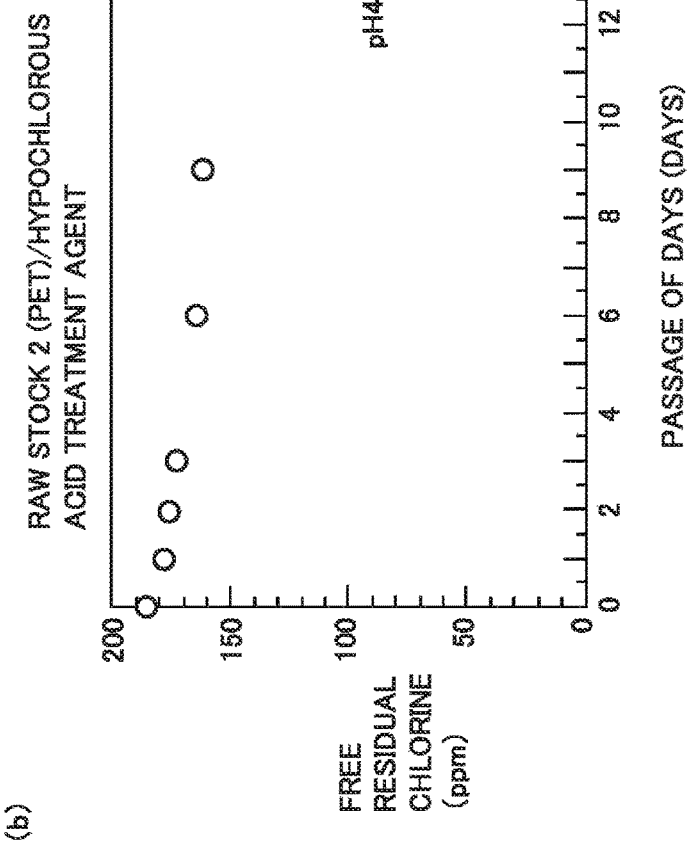
(b)
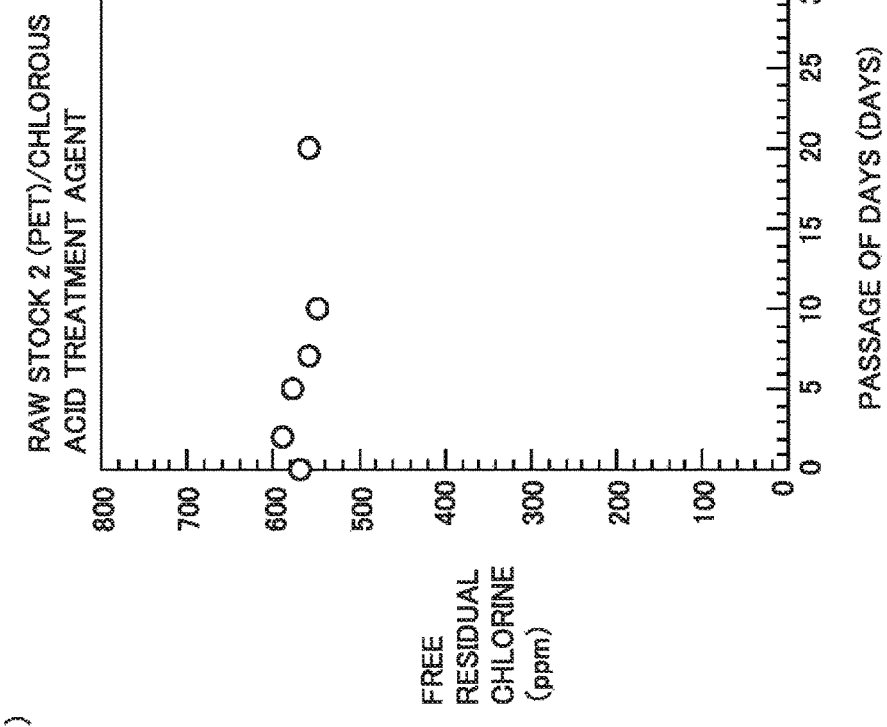

FIG.3
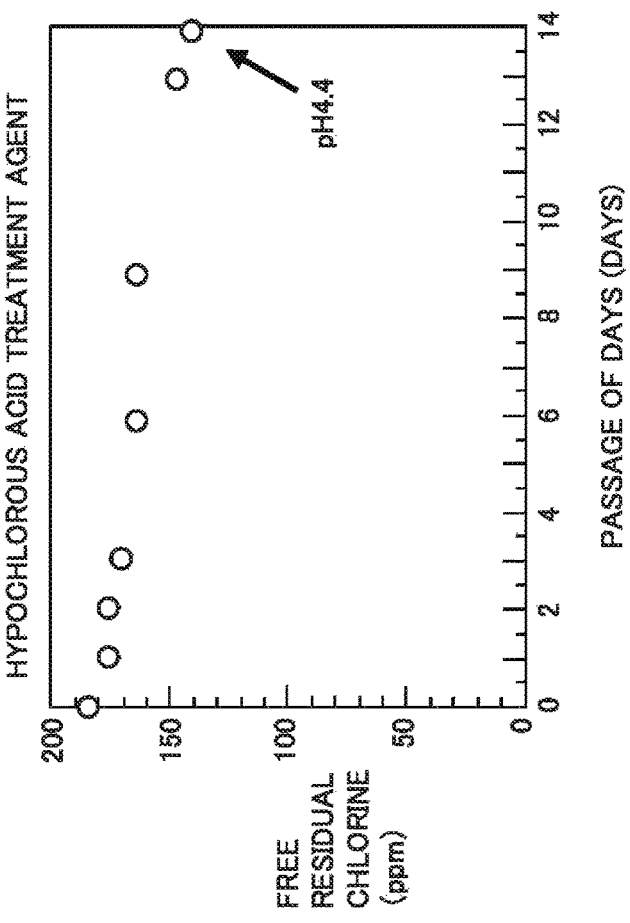
(b)
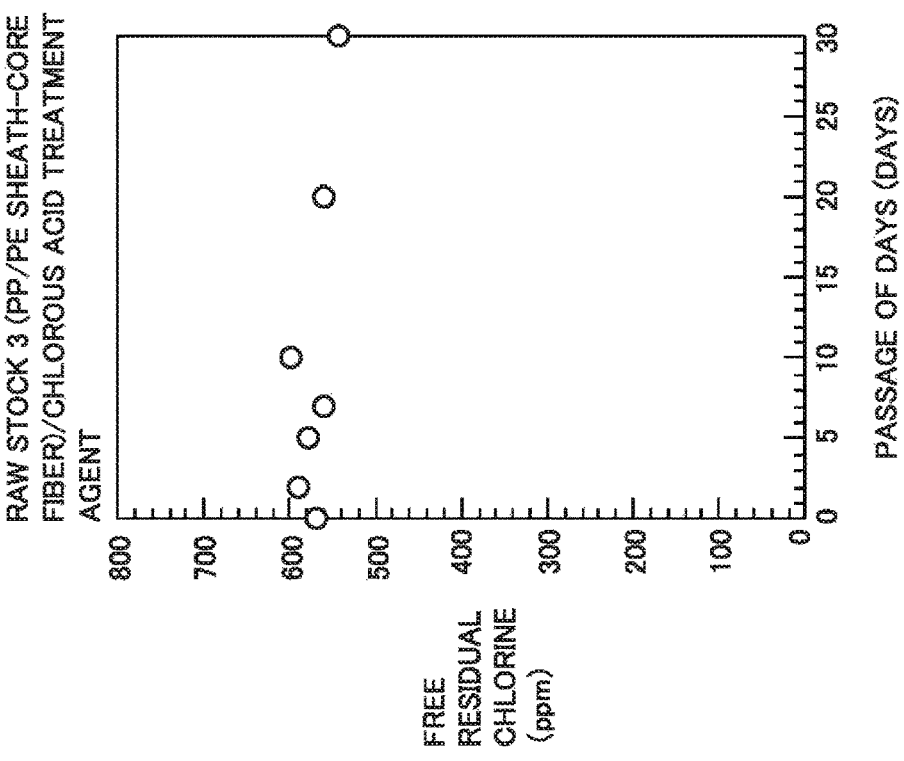
(a)

FIG.6
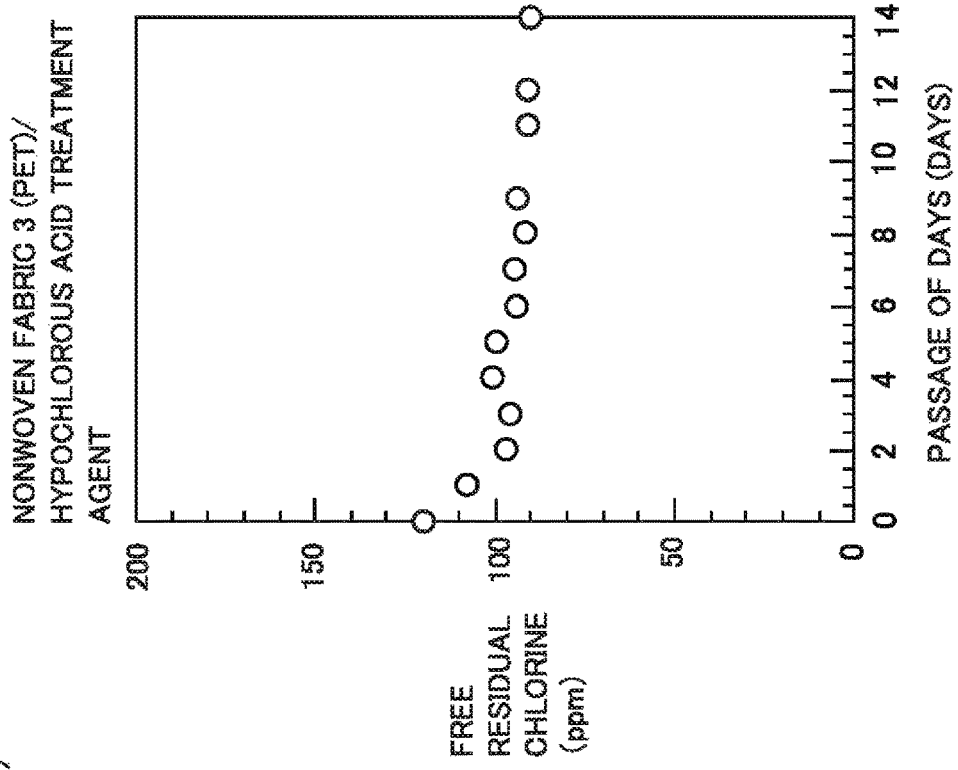
(b)
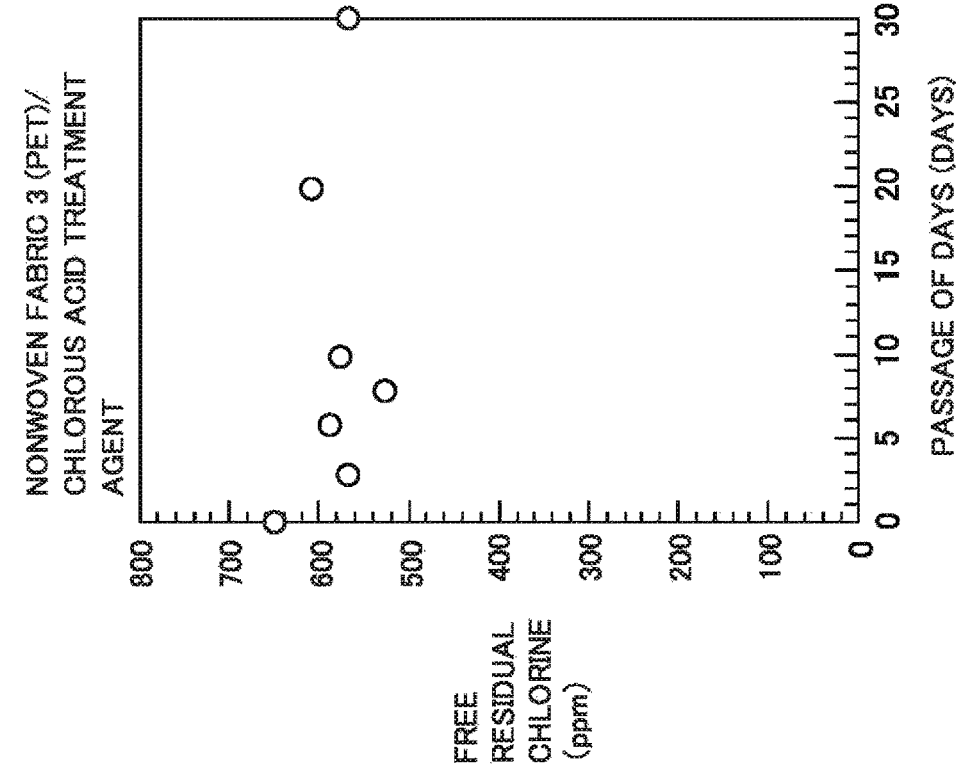
(a)

FIG.7
(a)
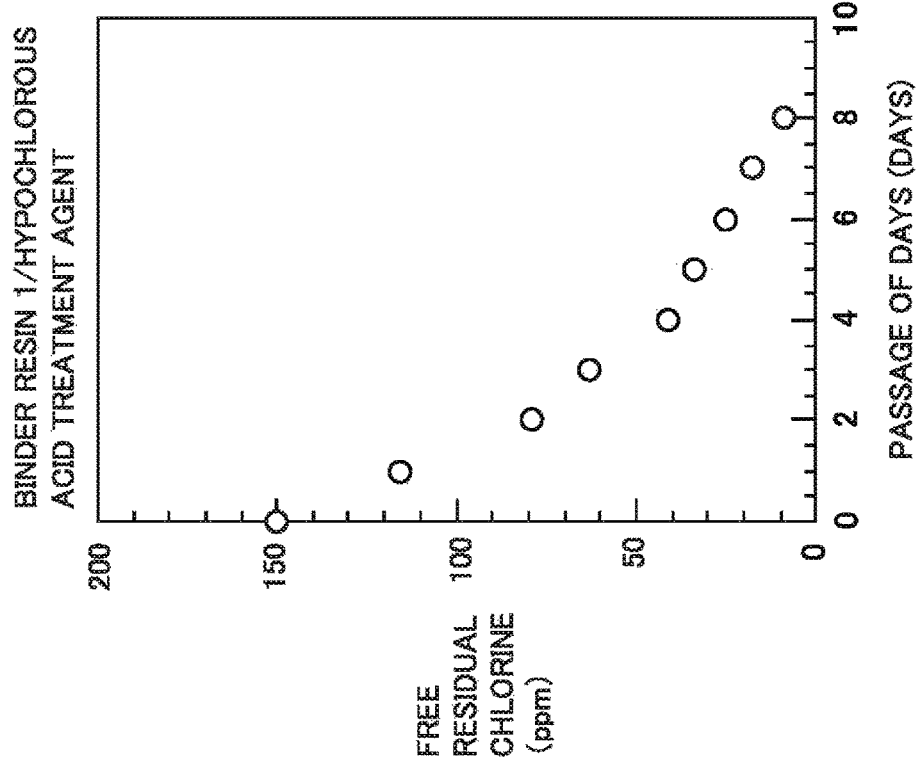
(b)
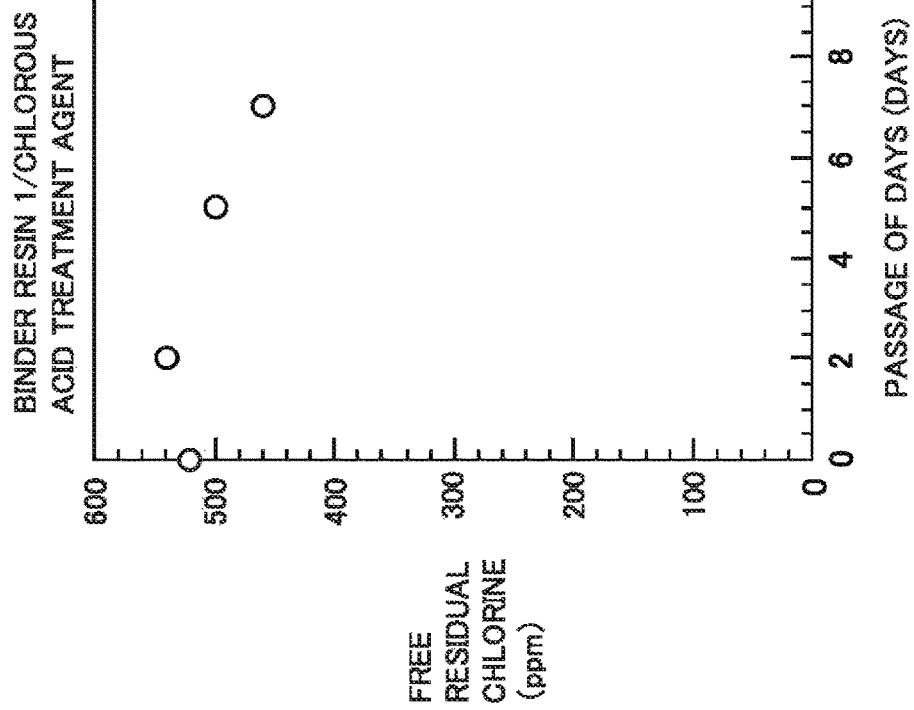

WET WIPER

TECHNICAL FIELD

The present invention relates to a wet wiper including a chlorine-based treatment agent.

BACKGROUND ART

A wet wiper used for the purpose of both wiping and sterilization has been known. Such a wet wiper, which is packaged with a fabric being impregnated with a microbicide, is convenient because after taking the wet wiper out from the package, the wet wiper can be used immediately without preparing the microbicide before each use.

As the microbicide in such a wet wiper, alcohol has been used conventionally. However, alcohol is insufficient in terms of an effect of inactivating viruses such as norovirus, disadvantageously. Moreover, alcohol is also insufficient in terms of a sterilization effect, disadvantageously. Further, the impregnation with alcohol leads to decrease in a degree of dissolving a contaminant constituted of water-soluble protein, saccharide, mineral salt, or the like, with the result that wiping efficiency is decreased, disadvantageously.

Japanese Patent Laying-Open No. 2015-110544 (Patent Literature 1) describes that a cotton treatment sheet impregnated with sodium hypochlorite and a cotton treatment sheet impregnated with chlorous acid water including a metal hydroxide and a metal phosphate are used for wiping.

CITATION LIST

Patent Literature

PTL 1: Japanese Patent Laying-Open No. 2015-110544

SUMMARY OF INVENTION

Technical Problem

Patent Literature 1 presents the following result: the cotton treatment sheet impregnated with sodium hypochlorite exhibits a sterilization effect immediately after the impregnation, but after storing the cotton treatment sheet for seven days, the sterilization effect is decreased (Tables 25 to 45). Moreover, Patent Literature 1 presents that the chlorous acid water including the metal hydroxide and the metal phosphate has a sterilization effect; however, a process of producing the chlorous acid water including the metal hydroxide and the metal phosphate is very complicated. Further, Patent Literature 1 presents that there is a sterilization effect when treating vomit on a floor surface using a wet sheet obtained by impregnating a treatment sheet with diluted chlorous acid water; however, there is no description as to efficiency of the wiper to wipe out a contaminant or microbe.

Meanwhile, the present inventors have conceived the following idea: if wet wipers can be colored, respective locations to be wiped by the wet wipers can be distinguished based on the colors, so that convenience of the wet wipers will be improved significantly. However, because a binder resin for binding a color material required for the coloring serves to decrease the effect of sodium hypochlorite, it is difficult to store such a wet wiper for a long period of time.

The present invention has an object to provide a novel wet wiper in which a sterilization effect and a wiping/cleaning effect are maintained even when the wet wiper is stored for a long period of time.

Solution to Problem

The present invention provides a wet wiper described below.

[1] A wet wiper including: a fabric; and a chlorine-based treatment agent included in the fabric, wherein the fabric is constituted of at least one fiber selected from a synthetic fiber, a semi-synthetic fiber, a regenerated fiber, and an inorganic fiber, and the chlorine-based treatment agent includes at least one of chlorous acid ($HClO_2$), chlorite ion ($ClO_2^-$), and chlorine dioxide ($ClO_2$) as an effective chlorine component.

[2] The wet wiper according to [1], wherein the wet wiper is accommodated in a package.

[3] The wet wiper according to [1] or [2], wherein the fabric includes the regenerated fiber.

[4] The wet wiper according to [3], wherein the regenerated fiber is at least one of rayon and lyocell.

[5] The wet wiper according to any one of [1] to [4], wherein the fabric is a nonwoven fabric.

[6] The wet wiper according to [5], wherein the nonwoven fabric is a short fiber nonwoven fabric having a fiber length of 18 to 110 mm.

[7] The wet wiper according to [5] or [6], wherein the nonwoven fabric has a weight of 20 to 200 $g/m^2$ and has a thickness of 0.2 to 1.5 mm.

[8] The wet wiper according to any one of [1] to [7], wherein the fabric is colored.

[9] The wet wiper according to any one of [1] to [8], wherein the fabric includes at least one binder resin selected from polyurethane, acrylic, polyethylene, polyolefin, a petroleum resin, asphalt, an isoprene-based hydrocarbon, a butadiene rubber, and vinyl chloride.

[10] The wet wiper according to [9], wherein the binder resin is a water-emulsifiable polymer.

Advantageous Effects of Invention

According to the present invention, there can be provided a novel wet wiper in which a sterilization effect and a wiping/cleaning effect are maintained even when the wet wiper is stored for a long period of time.

BRIEF DESCRIPTION OF DRAWINGS

FIG. 1 (a) shows a result of measurement of a concentration of free residual chlorine in a test example 1, and FIG. 1 (b) shows a result of measurement of a concentration of free residual chlorine in a test example 8.

FIG. 2 (a) shows a result of measurement of a concentration of free residual chlorine in a test example 2, and FIG. 2 (b) shows a result of measurement of a concentration of free residual chlorine in a test example 9.

FIG. 3 (a) shows a result of measurement of a concentration of free residual chlorine in a test example 3, and FIG. 3 (b) shows a result of measurement of a concentration of free residual chlorine in a test example 10.

FIG. 6 (a) shows a result of measurement of a concentration of free residual chlorine in a test example 6, and FIG. 6 (b) shows a result of measurement of a concentration of free residual chlorine in a test example 13.

FIG. 7 (a) shows a result of measurement of a concentration of free residual chlorine in a test example 7, and FIG. 7 (b) shows a result of measurement of a concentration of free residual chlorine in a test example 14.

DESCRIPTION OF EMBODIMENTS

Figure 4:
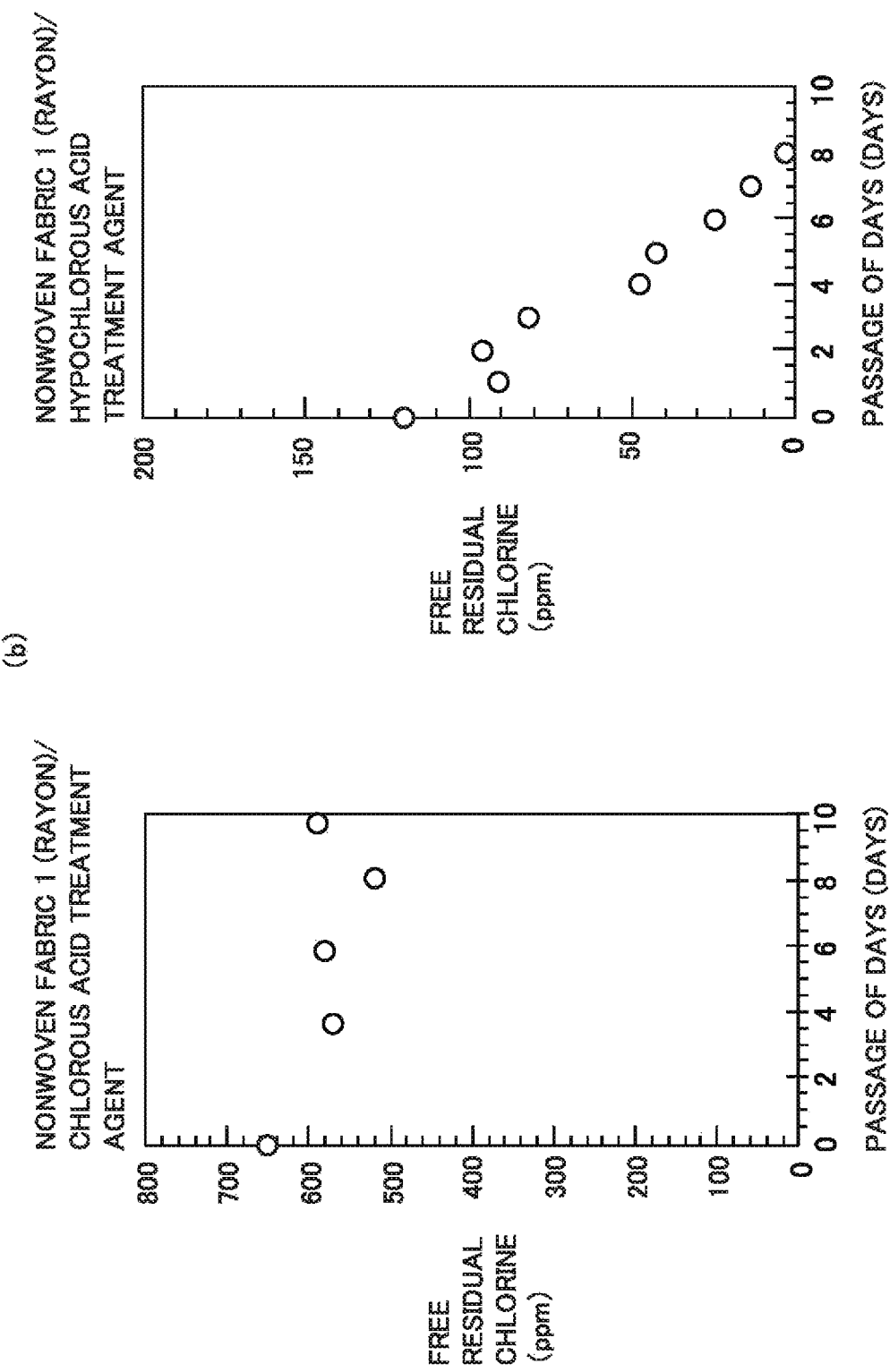
FIG. 4 (a) shows a result of measurement of a concentration of free residual chlorine in a test example 4, and FIG. 4 (b) shows a result of measurement of a concentration of free residual chlorine in a test example 11.

A wet wiper of the present invention includes: a fabric; and a chlorine-based treatment agent included in the fabric, wherein the chlorine-based treatment agent includes at least one of chlorous acid and chlorite ion as an effective chlorine component.

<Chlorine-Based Treatment Agent>

By way of the effective chlorine component, the chlorine-based treatment agent exhibits effects of sterilization, disinfection, and bleaching (hereinafter, referred to as "sterilization and the like") as well as an effect of wiping/cleaning. In the present invention, the chlorine-based treatment agent includes at least one of chlorous acid ($HClO_2$), chlorite ion ($ClO_2^-$), and chlorine dioxide ($ClO_2$) as the effective chlorine component, and preferably includes the chlorous acid ($HClO_2$) and the chlorite ion ($ClO_2^-$). The chlorous acid ($HClO_2$) and the chlorite ion ($ClO_2^-$) are suitable because they have a high sterilization effect.

Examples of such a chlorine-based treatment agent include a solution in which a chlorite, such as sodium chlorite or potassium chlorite, or chlorous acid is dissolved in a solvent. The pH of the solution is preferably 2.0 to 7.0, is more preferably 3.0 to 5.0, and is further preferably 3.5 to 4.5. Depending on the pH of the solution, a ratio of presence of chlorous acid ($HClO_2$), chlorite ion ($ClO_2^-$), and chlorine dioxide ($ClO_2$) is changed. The pH of the solution preferably falls within a range of 2.0 to 7.0 because undissociated chlorous acid ($HClO_2$), which has a high sterilization effect, and chlorite ion ($ClO_2^-$), which is highly stable, are present in good balance.

Examples of the solvent include water, a nonaqueous solvent, and the like. Examples of the nonaqueous solvent include: a glycol such as propylene glycol, butylene glycol, triethylene glycol, hexylene glycol, polyethylene glycol, ethoxydiglycol, and dipropylene glycol; an alcohol such as ethanol, n-propanol, and isopropanol; triglyceride, ethyl acetate, acetone, and triacetin; and a combination thereof.

The chlorine-based treatment agent may include a surfactant, a chelating agent, an antiseptic agent, a colorant, a flavoring agent, a stabilizer, and the like.

The content of the effective chlorine component in the chlorine-based treatment agent is preferably more than or equal to 50 ppm, is more preferably more than or equal to 100 ppm, and is further preferably more than or equal to 500 ppm. Since the content of the effective chlorine component is more than or equal to 50 ppm, performance in sterilization and the like is more improved. Furthermore, when the content of the effective chlorine component is more than or equal to 500 ppm, cleaning power is more improved. Moreover, the content of the effective chlorine component is preferably less than or equal to 1000 ppm because skin irritation can be suppressed.

The content of the chlorine-based treatment agent in the wet wiper is preferably more than or equal to 100 parts by mass, is more preferably more than or equal to 200 parts by mass, and is further preferably more than or equal to 300 parts by mass with respect to 100 parts by mass of the fabric. Since the content of the chlorine-based treatment agent in the wet wiper is more than or equal to 100 parts by mass, performance in sterilization and the like is more improved. On the other hand, the content of the chlorine-based treatment agent in the wet wiper is preferably less than or equal to 1000 parts by mass, is more preferably less than or equal to 800 parts by mass, and is further preferably less than or equal to 700 parts by mass with respect to 100 parts by mass of the fabric. Since the content of the chlorine-based treatment agent in the wet wiper is less than or equal to 1000 parts by mass, workability in wiping with the wet wiper can be suppressed from being decreased. The chlorine-based treatment agent is preferably uniformly included in the fabric.

Since the chlorine-based treatment agent including at least one of chlorous acid ($HClO_2$), chlorite ion ($ClO_2^-$), and chlorine dioxide ($ClO_2$) as the effective chlorine component is used in the wet wiper of the present invention, the efficacy of sterilization and the like is maintained even when the wet wiper is stored for a long period of time. Even when the wet wiper is stored for a long period of time, for example, 30 days or longer, the efficacy of sterilization and the like is maintained. Moreover, since the efficacy of sterilization and the like is maintained, microbes caught in the fabric of the wet wiper as a result of wiping are less likely to be grown, thus preventing recontamination of a wiped object.

The chlorine-based treatment agent including at least one of chlorous acid ($HClO_2$), chlorite ion ($ClO_2^-$), and chlorine dioxide ($ClO_2$) as the effective chlorine component as used in the present invention has low reactivity with the fabric, and is less likely to be consumed even when the chlorine-based treatment agent is stored in contact with the fabric. Hence, the efficacy of sterilization and the like is maintained even when stored for a long period of time. On the other hand, as a result of examination by the present inventors, it has been found that when a wet wiper is produced using hypochlorous acid (HClO) or hypochlorite ion ($ClO^-$) as the effective chlorine component, the hypochlorous acid (HClO) or hypochlorite ion ($ClO^-$) reacts with a fiber or binder resin included in a fabric, with the result that the sterilization effect is decreased with passage of time.

Moreover, since the strength of the fabric is maintained even when the wet wiper of the present invention is stored for a long period of time, it is possible to suppress wiping workability from being decreased, suppress wiping strength from being decreased, and suppress a wiped object from being contaminated by a matter from the fabric. Each of these would have been otherwise caused by decreased strength of the fabric.

<Fabric>

The fabric is constituted of at least one fiber selected from a synthetic fiber, a semi-synthetic fiber, a regenerated fiber, and an inorganic fiber.

The synthetic fiber is, for example, a fiber composed of at least one synthetic resin selected from known fiber-forming resins such as: polyester resins, such as polyethylene terephthalate, polytrimethylene terephthalate, polybutylene terephthalate, and a polyester elastomer; acrylic resins and olefine resins; and polyamide resins such as Nylon 6, Nylon 66, Nylon 610, aromatic polyamide, and a polyamide elastomer; polyvinyl alcohol resins; and polyurethane-based, polyolefin-based, acrylonitrile-based and similar polymers, each of which has a fiber forming ability, and modified resins thereof.

Examples of the semi-synthetic fiber include acetate, triacetate, and the like. Examples of the regenerated fiber include rayon, lyocell, cupra, Tencel®, and the like. Examples of the inorganic fiber include glass fiber, carbon fiber, and the like.

Among these, the regenerated fiber is preferably included because the regenerated fiber is excellent in liquid absorbency, liquid retention, and contaminant scratching performance. At least one of rayon and lyocell is preferably included. Moreover, the regenerated fiber is preferable also because the regenerated fiber has low reactivity with the chlorine-based treatment agent used in the present invention and can maintain the efficacy of sterilization and the like even when it is stored for a long period of time.

The fiber may be one of a general fiber, a hollow fiber, a modified cross-section fiber, and a microfine fiber. A colorant, an ultraviolet absorber, a thermostabilizer, a deodorizer, an antifungal agent, an antimicrobial agent, various types of stabilizers, and the like may be added to the fiber.

When the fiber is a synthetic fiber, the fiber can be formed in accordance with: a melt spinning method in which a yarn is formed by melting a resin at a temperature more than or equal to its melting point and extruding it from an extruder; a dry type solution spinning method in which a polymer solution is pushed out from a pore and a solvent is evaporated; or a wet type solution spinning in which the polymer solution is formed into a yarn in a non-solvent.

When the fiber is a microfine fiber, the fabric may be formed from a microfine-fiber-forming fiber and then may be processed to be microfine, or may be formed directly from a microfine fiber. Examples of the microfine-fiber-forming fiber include an islands-in-the-sea fiber, a multilayer stack-type fiber, a radial stack-type fiber, and the like. When the fabric is a nonwoven fabric, the islands-in-the-sea fiber is preferable because the islands-in-the-sea fiber is less damaged upon needle punching and attains uniformity in a degree of fineness of the microfine fiber. Although the following describes an example in which the islands-in-the-sea fiber is used as the microfine-fiber-forming fiber; however, below-described steps may be performed using a different fabric and a different microfine-fiber-forming fiber, such as the multilayer stack-type fiber, the radial stack-type fiber, or the like.

The islands-in-the-sea fiber is a multi-component composite fiber composed of at least two types of polymers, and has a cross section in which an island-component polymer different in type from a sea-component polymer (removable polymer) is dispersed in the sea-component polymer. The sea-component polymer is extracted or decomposed and is accordingly removed, whereby the islands-in-the-sea fiber is converted into a fiber bundle including a plurality of gathered microfine fibers constituted of the remaining island-component polymer.

An islands-in-the-sea fiber may be used in which the sea-component and the island-component are reversed. That is, an islands-in-the-sea fiber may be used in which the sea-component polymer is the resin constituting the fiber and the island-component polymer is the removable polymer. By extracting or decomposing and accordingly removing the island-component polymer, the islands-in-the-sea fiber is converted into a porous hollow fiber constituted of the remaining sea-component polymer.

A method for forming the fiber into the fabric is not particularly limited, and any of weaving, knitting, and non-weaving may be employed. Examples of the weaving mainly include a method in which warp and weft are interwoven in a certain pattern, such as plain weaving, twill weaving, satin weaving, or the like. Alternatively, a knitting method may be employed in which stitches are put one after another in such a manner as to make knots.

In the case of non-weaving, the fiber is extended and crimped, and then is cut into a certain fiber length (18 to 110 mm) to obtain a staple, which is then formed into a short fiber nonwoven fabric using a card, a crosslapper, a random webber, an entangling device, and the like. Alternatively, a method, such as a melt blowing method or a flash spinning method, can be used, in which a fiber is thinned by blowing, with a high-speed gas, a fiber-forming polymer immediately after discharging the fiber-forming polymer from a melt-spinning nozzle. Alternatively, a nanofiber may be formed using an electro-spinning method or a paper-making method. Further, a long fiber formed by using a spun-bond method or the like may be accumulated on a capturing surface of a movable net or the like without being cut, thereby forming a long nonwoven fabric substantially constituted of an unextended long fiber. Moreover, as required, at least one or more types of fabrics produced by the above-mentioned methods can be placed into a plurality of layers to overlap with one another using a crosslapper or the like, and can be then entangled by needle punching, high-speed fluid, high-temperature fluid, or the like, thereby producing a fabric having a high weight, a high specific gravity or an excellent shape retention property. The obtained fabric preferably has a weight of 10 to 1000 $g/m^2$, and may include a high-polymer elastomer in the fabric or on a surface of the fabric.

As the fabric of the present invention, a short fiber nonwoven fabric having a fiber length of 18 to 110 mm is preferable in order to efficiently remove a contaminant and improve a wiping property. Moreover, the weight of the nonwoven fabric is preferably 20 to 200 $g/m^2$, and is more preferably 30 to 150 $g/m^2$. The thickness of the nonwoven fabric is preferably 0.2 to 1.5 mm, and is more preferably 0.2 to 1.0 mm. These ranges of the weight and thickness are preferable because when the weight and thickness fall within these respective ranges, the resultant wet wiper has softness with which the wet wiper can be folded readily for use and can be readily changed in shape with force of a hand along a wiped object.

The fabric of the present invention may be colored. Since the fabric is colored, a contaminant can be readily recognized visually when wiping out a contaminant using the wet wiper, advantageously. Moreover, since the fabric is colored, the wet wiper can be distinguished by the color, advantageously. In this case, for example, a location to be wiped by the wet wiper can be distinguished in accordance with the color of the wet wiper. Although a coloring method is not limited particularly, an exemplary coloring method is to adhere a colorant to the surface of the fiber of the fabric by way of the binder resin. According to the wet wiper of the present invention, even though the fabric includes the binder resin, the efficacy of sterilization and the like is maintained.

Examples of the colorant used to color the fabric include: pigments such as hydrozincite, white lead, titanium dioxide, barium sulfate, minium, iron oxide, zinc yellow, ultramarine blue, prussian blue, phthalocyanine, ferrocyanide, and ferricyanide; and biological substances such as hemoglobin or chlorophyll. Among these, a complex including cyanide ion in a ligand is particularly suitably used due to its excellent coloring property. More preferably, the ferrocyanide or ferricyanide is used. Examples thereof include iron (II) hexacyanoferrate (III), iron (III) hexacyanoferrate (II) (ferric ferrocyanide), ferric ammonium ferrocyanide, copper ferrocyanide, silver ferrocyanide, iron blue, and the like. Examples of the binder resin include polyurethane, acrylic, polyethylene, polyolefin, a petroleum resin, asphalt, an isoprene-based hydrocarbon, a butadiene rubber, vinyl chloride, and the like. Among these, a water-emulsifiable polycarbonate-based polyurethane elastomer, an acrylic polymer containing a soft component and a hard component, and an isoprene-based hydrocarbon are used particularly preferably. Moreover, the binder resin is preferably a water-emulsifiable polymer because the water-emulsifiable polymer is likely to be adhered in the form of fine particles.

<Package>

The wet wiper of the present invention is preferably accommodated in a package. Although the package is not particularly limited, the package is preferably composed of a material that can suppress volatilization of the chlorine-based treatment agent and that has high resistance against the chlorine-based treatment agent. As a form of the package, it is suitable to use a package provided with an opening covered with a cover that can be repeatedly opened and closed. By way of example, a plurality of such wet wipers are folded, piled up, and accommodated in such a package.

A wet wiper accommodated in a package is generally stored for a long period of time before being used. According to the wet wiper of the present invention, the sterilization effect is maintained even when the wet wiper is stored for a period of 1 year or longer.

<Method for Manufacturing Wet Wiper>

A method for manufacturing the wet wiper is not particularly limited. An exemplary manufacturing method is a method including the steps of: producing the fabric as described above; preparing the chlorine-based treatment agent; impregnating the fabric with the chlorine-based treatment agent; and accommodating the wet wiper in the package and sealing the package.

<Application>

The wet wiper of the present invention can be used for various wiping targets and wiped objects. Examples of the wiping targets include blood, body fluid, bacteria, fungus, virus, and other biological substances. The wet wiper of the present invention can be used to wipe them out for the purpose of sterilization, sanitization, inactivation, and disinfection. Other examples of the wiping targets include fat, protein, and oil spots. The wet wiper of the present invention can be used to wipe them out for the purpose of cleaning.

The wiped object is not limited particularly. Examples of the wiped object include facilities, apparatuses (devices, instruments, touch panels, control panels, handrails, and the like), furniture, small articles, floors or walls, and hand fingers. Particularly, the wet wiper of the present invention can be suitably used for facilities and apparatuses, which cannot be washed with water, in food manufacturing sites and medical sites.

According to the wet wiper of the present invention, the sterilization effect and the wiping/cleaning effect are maintained even when the wet wiper is stored for a long period of time. Moreover, since the efficacy of sterilization and the like is maintained, microbes caught in the fabric of the wet wiper as a result of wiping are less likely to be grown, thus preventing recontamination of the wiped object.

EXAMPLES

[Preparation of Samples]

<Preparation of Chlorine-Based Treatment Agent 1 (Chlorous Acid Treatment Agent)>

As a chlorine-based treatment agent 1, a sodium chlorite ($NaClO_2$) aqueous solution was prepared.

<Preparation of Chlorine-Based Treatment Agent 2 (Hypochlorous Acid Treatment Agent)>

As a chlorine-based treatment agent 2, a sodium hypochlorite (NaClO) aqueous solution was prepared.

<Preparation of Alcohol-Based Disinfectant 1>

As an alcohol-based disinfectant 1, an aqueous solution with 70% of ethanol was prepared.

<Preparation of Raw Stocks of Fibers, Nonwoven Fabrics, Binder Resin, and Chips Each Serving as Impregnation Target>

Below-described raw stocks 1 to 3, nonwoven fabrics 1 to 4, binder resin 1, and chips 1 and 2 were prepared. Each of raw stocks 1 to 3 can be used as a material of a fabric of a wet wiper. Each of nonwoven fabrics 1 to 4 can be used as the fabric of the wet wiper itself. Each of chips 1 and 2 can be used as a resin material for the fabric of the wet wiper. Binder resin 1 can be used as a material for coloring the fabric.

Raw stock 1: rayon raw stock (degree of fineness of 1.7 dtex; fiber length of 40 mm)

Raw stock 2: polyethylene terephthalate raw stock (degree of fineness of 1.7 dtex; fiber length of 51 mm)

Raw stock 3: polypropylene/polyethylene sheath-core fiber (degree of fineness of 1.7 dtex; fiber length of 51 mm)

Nonwoven fabric 1: rayon nonwoven fabric (80 mass % of rayon; degree of fineness of 1.7 dtex; fiber length of 40 mm; weight of 60 g/m$^2$; thickness of 0.50 mm)

Nonwoven fabric 2: lyocell nonwoven fabric (100 mass % of lyocell; degree of fineness of 1.7 dtex; fiber length of 38 mm; weight of 60 g/m$^2$; thickness of 0.53 mm)

Nonwoven fabric 3: polyethylene terephthalate nonwoven fabric (100 mass of polyethylene terephthalate; degree of fineness of 1.7 dtex; fiber length of 51 mm; weight of 60 g/m$^2$; thickness of 0.65 mm)

Binder resin 1: water-emulsifiable acrylic ester copolymer

Chip 1: ethylene-vinylalcohol copolymer chip (trademark: EVAL E112 provided by Kuraray)

Chip 2: polyvinyl alcohol chip (trademark: POVAL 105 provided by Kuraray)

Nonwoven fabric 4: rayon nonwoven fabric (provided by Kuraray Kuraflex; 80 mass % of rayon; degree of fineness of 1.7 dtex; fiber length of 40 mm; 20 mass % of the binder resin (water-emulsifiable acrylic ester copolymer); weight of 76 g/m$^2$; thickness of 0.57 mm).

Evaluation Tests

Test Examples 1 to 7: Change in Concentration of Effective Chlorine Component of Chlorine-Based Treatment Agent 1 with Passage of Time 2.0 g of each impregnation target shown in Table 1 was introduced into 100 ml of chlorine-based treatment agent 1, was shielded from light, was maintained at 20° C., and was continuously stirred (300 rpm) using a stirrer. The concentration and pH of the sodium chlorite ($NaClO_2$) of chlorine-based treatment agent 1 were adjusted as shown in Table 1. The concentration of free residual chlorine of chlorine-based treatment agent 1 was measured by the sodium chlorite DPD colorimetric method in a period from a time immediately after the introduction to predetermined days (any of 10 days, 14 days, and 30 days) after the introduction. In each of test examples 1 to 7, the concentration of the free residual chlorine as measured by the potassium iodide/DPD colorimetric method is a total concentration of chlorous acid (HClO$_2$) and chlorite ion (ClO$_2^-$), each of which is the effective chlorine component.

Test Examples 8 to 16: Change in Concentration of Effective Chlorine Component of Chlorine-Based Treatment Agent 2 with Passage of Time 2.0 g of each impregnation target shown in Table 1 was introduced into 100 ml of chlorine-based treatment agent 2, was shielded from light, was maintained at 20° C., and was continuously stirred (300 rpm) using a stirrer. The concentration and pH of the sodium hypochlorite (NaClO) of chlorine-based treatment agent 2 were adjusted as shown in Table 1. In a period from a time immediately after the introduction to 14 days after the introduction, the concentration of the free residual chlorine of chlorine-based treatment agent 2 was measured by the DPD colorimetric method. In each of test examples 8 to 16, the concentration of free residual chlorine as measured by the DPD colorimetric method is a total concentration of hypochlorous acid (HClO) and hypochlorite ion (ClO$^-$), each of which is the effective chlorine component.

acid treatment agent) after passage of 14 days from the introduction thereof.

Test Example 17: Checking for Sterilization Effect

Each of nonwoven fabrics 4 was sterilized by being irradiated with ultraviolet ray in 2 hours within a clean bench. Each of nonwoven fabrics 4 (50 mm×50 mm) was placed on a polyethylene film (60 mm×60 mm) placed on a sterilized Petri dish. Each of the nonwoven fabrics was impregnated with 0.6 ml of a test liquid (physiological saline solution (control), chlorine-based treatment agent 1 (600 ppm of NaClO$_2$; pH of 4.0), chlorine-based treatment agent 2 (200 ppm of NaClO; pH of 6.0), or an alcohol-based disinfectant 1) by dropping the test liquid onto the nonwoven fabric. Then, the Petri dish was covered and was settled at 25° C. for 6 hours. In order to prevent volatilization of the liquid therein, 0.5 ml of physiological saline solution was put at a corner of the Petri dish. After passage of 6 hours, 0.3 ml of a microbe liquid (supplied microbe: *Staphylococcus aureus* NBRC 12732) was dropped onto the nonwoven fabric, and the Petri dish was covered and settled at 25° C. for 1 hour. After passage of 1 hour, 10 ml of physiological saline solution (containing 3 mass % of Na$_2$S$_2$O$_3$) including Tween 80 at a concentration of 0.7 mass % was introduced to wash out the microbe from the nonwoven fabric. 0.1 ml

TABLE 1

Figure 5:
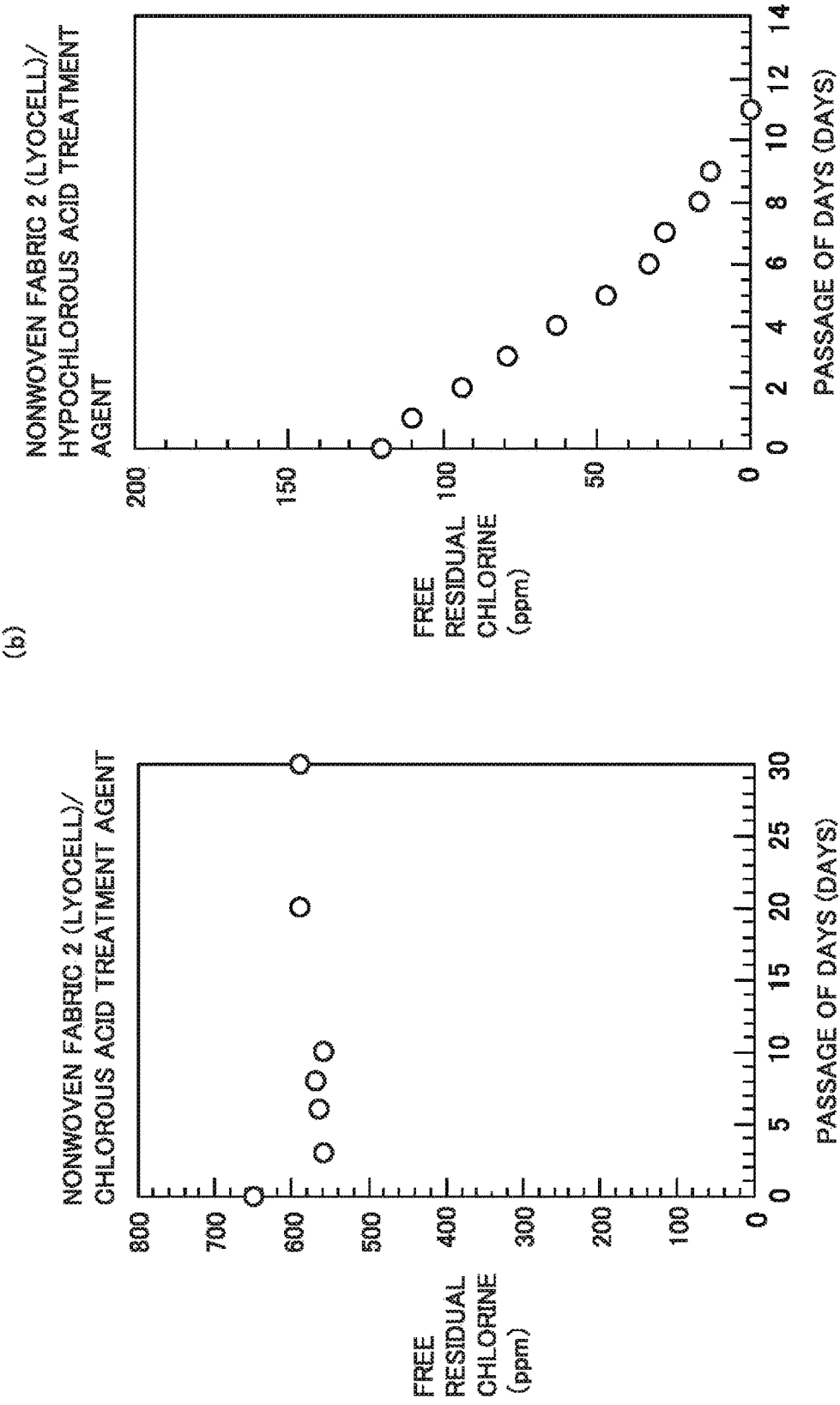
FIG. 5 (a) shows a result of measurement of a concentration of free residual chlorine in a test example 5, and FIG. 5 (b) shows a result of measurement of a concentration of free residual chlorine in a test example 12.
Figure 8:
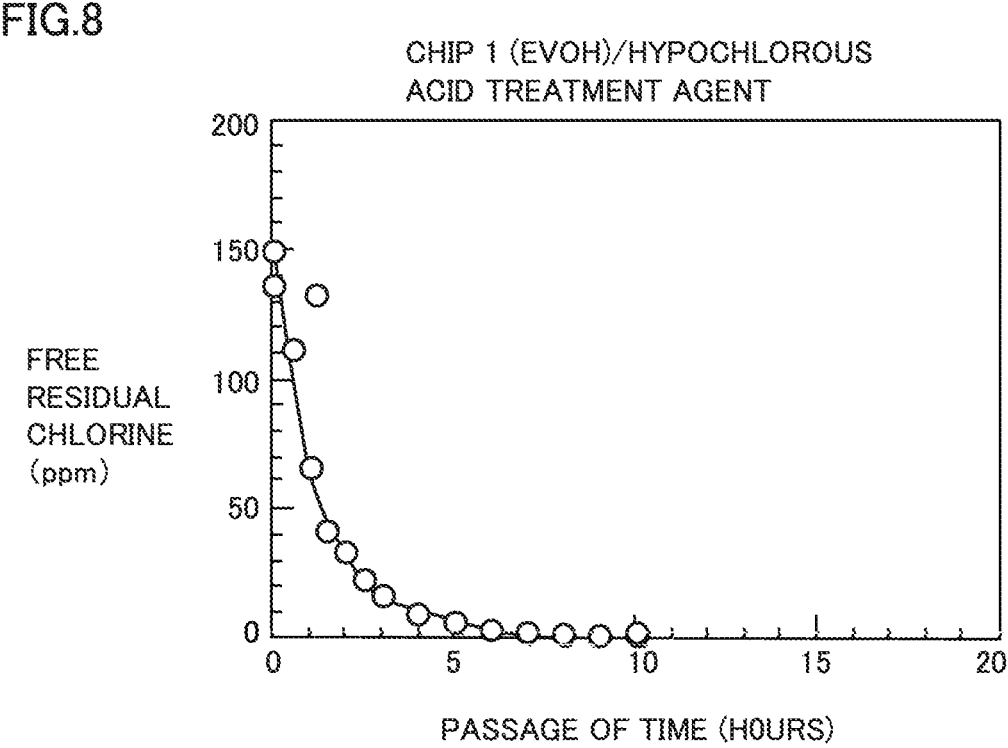
FIG. 8 shows a result of measurement of a concentration of free residual chlorine in a test example 15.
Figure 9:
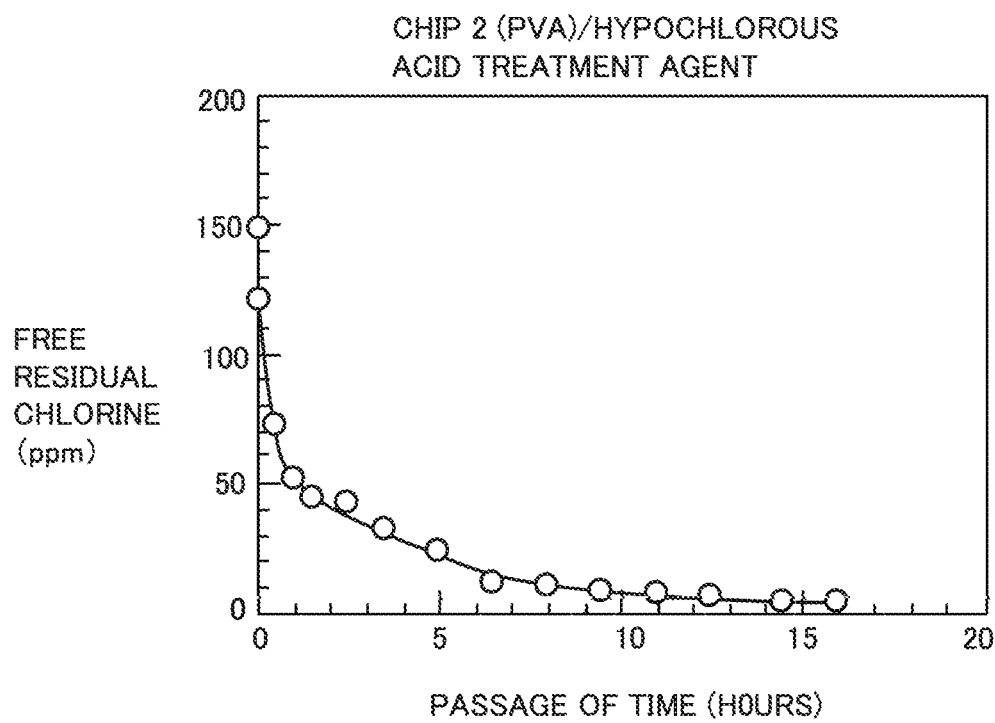
FIG. 9 shows a result of measurement of a concentration of free residual chlorine in a test example 16.

| Test Example | Chlorine-Based Treatment Agent Type | Concentration | pH | Impregnation Target | Test Result |
|---|---|---|---|---|---|
| Test Example 1 | Chlorine-Based Treatment Agent 1 (Chlorous Acid Treatment Agent) | 570 ppm | 4.0 | Raw Stock 1 (Rayon) | FIG. 1 (a) |
| Test Example 2 | Chlorine-Based Treatment Agent 1 (Chlorous Acid Treatment Agent) | 570 ppm | 4.0 | Raw Stock 2 (PET) | FIG. 2 (a) |
| Test Example 3 | Chlorine-Based Treatment Agent 1 (Chlorous Acid Treatment Agent) | 570 ppm | 4.0 | Raw Stock 3 (PP/PE) | FIG. 3 (a) |
| Test Example 4 | Chlorine-Based Treatment Agent 1 (Chlorous Acid Treatment Agent) | 650 ppm | 4.0 | Nonwoven Fabric 1 (Rayon) | FIG. 4 (a) |
| Test Example 5 | Chlorine-Based Treatment Agent 1 (Chlorous Acid Treatment Agent) | 650 ppm | 4.0 | Nonwoven Fabric 2 (Lyocell) | FIG. 5 (a) |
| Test Example 6 | Chlorine-Based Treatment Agent 1 (Chlorous Acid Treatment Agent) | 650 ppm | 4.0 | Nonwoven Fabric 3 (PET) | FIG. 6 (a) |
| Test Example 7 | Chlorine-Based Treatment Agent 1 (Chlorous Acid Treatment Agent) | 500 ppm | 4.0 | Binder 1 | FIG. 7 (a) |
| Test Example 8 | Chlorine-Based Treatment Agent 2 (Hypochlorous Acid Treatment Agent) | 186 ppm | 6.0 | Raw Stock 1 (Rayon) | FIG. 1 (b) |
| Test Example 9 | Chlorine-Based Treatment Agent 2 (Hypochlorous Acid Treatment Agent) | 186 ppm | 6.0 | Raw Stock 2 (PET) | FIG. 2 (b) |
| Test Example 10 | Chlorine-Based Treatment Agent 2 (Hypochlorous Acid Treatment Agent) | 180 ppm | 6.0 | Raw Stock 3 (PP/PE) | FIG. 3 (b) |
| Test Example 11 | Chlorine-Based Treatment Agent 2 (Hypochlorous Acid Treatment Agent) | 186 ppm | 6.0 | Nonwoven Fabric 1 (Rayon) | FIG. 4 (b) |
| Test Example 12 | Chlorine-Based Treatment Agent 2 (Hypochlorous Acid Treatment Agent) | 186 ppm | 6.0 | Nonwoven Fabric 2 (Lyocell) | FIG. 5 (b) |
| Test Example 13 | Chlorine-Based Treatment Agent 2 (Hypochlorous Acid Treatment Agent) | 186 ppm | 6.0 | Nonwoven Fabric 3 (PET) | FIG. 6 (b) |
| Test Example 14 | Chlorine-Based Treatment Agent 2 (Hypochlorous Acid Treatment Agent) | 150 ppm | 5.0 | Binder Resin 1 | FIG. 7 (b) |
| Test Example 15 | Chlorine-Based Treatment Agent 2 (Hypochlorous Acid Treatment Agent) | 150 ppm | 6.0 | Chip 1 (EVOH) | FIG. 8 |
| Test Example 16 | Chlorine-Based Treatment Agent 2 (Hypochlorous Acid Treatment Agent) | 150 ppm | 5.0 | Chip 2 (PVA) | FIG. 9 |

Results of test examples 1 to 16 are shown in FIGS. 1 to 9. Each of notations with "/" in FIGS. 1 to 9 indicates "impregnation target/chlorine-based treatment agent". Moreover, each of FIG. 1 (b) to FIG. 3 (b) shows the pH value of chlorine-based treatment agent 2 (hypochlorous acid treatment agent) after passage of 14 days from the introduction thereof.

of the liquid having washed out was sampled to produce a 10× dilution series, and an agar plate method was employed to measure the number of living microbes based on the number of formed colonies. A log reduction value of the number of living microbes as compared with that in the nonwoven fabric impregnated with the physiological saline solution (control) was calculated, and was regarded as an antimicrobial activity value. An antimicrobial activity value of more than or equal to 2.0 is an index representing antimicrobial activity. Results are shown in Table 2.

Test Example 18: Checking for Sterilization Effect

A test was conducted in the same manner as in test example 17 except that each of test liquids used in test example 18 contained 0.2 mass % of polypeptone added to the physiological saline solution (control), chlorine-based treatment agent 1 (600 ppm of $NaClO_2$; pH of 4.0), chlorine-based treatment agent 2 (200 ppm of NaClO; pH of 6.0), or alcohol-based disinfectant 1. Then, the number of living microbes was measured to calculate an antimicrobial activity value. Here, the polypeptone was added as a pseudo contaminant. Results are shown in Table 2.

TABLE 2

| | Test Liquid | | Evaluation | |
|---|---|---|---|---|
| | Type | Addition of Polypeptone | the Number of Living Microbes | Anti-microbial Activity Value |
| Test Example 17 | Physiological Saline Solution (Control) | Not Added | $4.3 \times 10^5$ | — |
| | Alcohol-Based Disinfectant 1 | Not Added | $5.1 \times 10^4$ | 0.93 |
| | Chlorine-Based Treatment Agent 2 (Hypochlorous Acid Treatment Agent) | Not Added | <100 | >3.6 |
| | Chlorine-Based Treatment Agent 1 (Chlorous Acid Treatment Agent) | Not Added | <100 | >3.6 |
| Test Example 18 | Physiological Saline Solution (Control) | Added | $1.2 \times 10^6$ | — |
| | Alcohol-Based Disinfectant 1 | Added | $4.9 \times 10^5$ | 0.39 |
| | Chlorine-Based Treatment Agent 2 (Hypochlorous Acid Treatment Agent) | Added | $2.7 \times 10^5$ | 0.65 |
| | Chlorine-Based Treatment Agent 1 (Chlorous Acid Treatment Agent) | Added | $1.1 \times 10^4$ | 2.0 |

Test Example 19: Checking for Wiping/Cleaning Effect

1. Preparation of Pseudo Contaminant (1) 0.9 ml of a casein sodium aqueous solution at 2.5% (w/v) and 0.1 ml of a curcumin ethanol solution at 0.2% (w/v) were mixed to obtain a contaminant source liquid.

(2) A micropipette was used to drop 1 μl of the contaminant source liquid onto a surface of a stainless steel plate.

(3) The stainless steel plate having the contaminant source liquid dropped thereon was dried in a drier at 120° C. for 2 hours, thereby preparing a pseudo contaminant.

2. Cleaning Experiment (1) As the fabric of the wiper, nonwoven fabric 1 (30 mm×30 mm) was used.

(2) As test liquids, there are prepared: a) distilled water; b) alcohol-based disinfectant 1; c) chlorine-based treatment agent 2 (200 ppm of NaClO; pH of 6.0); and d) chlorine-based treatment agent 1 (600 ppm of $NaClO_2$; pH of 4.0).

(3) Each of a fabric impregnated with no test liquid and fabrics impregnated with 0.2 ml of respective test liquids was used to wipe out the pseudo contaminant on the stainless steel plate at a pressing force of about 200 gf.

3. Quantification of Remaining Contaminant

The mass (W0) of the pseudo contaminant on the surface of the stainless steel plate before the wiping and the mass (W1) of the pseudo contaminant on the surface of the stainless steel plate after the wiping were quantified to calculate a pseudo contaminant removal ratio. The pseudo contaminant removal ratio was calculated based on the following formula:

Removal ratio (%)={(W0−W1)/W0}×100

Results are shown in Table 3. The quantification of the pseudo contaminant for calculating the removal ratio was performed using a fluorescence detection method with curcumin serving as an index. Curcumin is a fluorescent dye.

TABLE 3

| | Test Liquid | Removal Ratio (%) |
|---|---|---|
| Test Example 19 | None | 0.5 |
| | Distilled Water | 65 |
| | Alcohol-Based Disinfectant 1 | 42 |
| | Chlorine-Based Treatment Agent 2 (Hypochlorous Acid Treatment Agent) | 67 |
| | Chlorine-Based Treatment Agent 1 (Chlorous Acid Treatment Agent) | 87 |

[Results]

As understood from FIG. 1 to FIG. 7, reactivity between chlorine-based treatment agent 1 (chlorous acid treatment agent) and the impregnation target was very low in each material, and the free residual chlorine concentration even after passage of 10 days from the introduction was maintained to be about 85 to 90 mass % relative to the free residual chlorine concentration at the time of the introduction (FIG. 1 (a) to FIG. 7 (a)). On the other hand, chlorine-based treatment agent 2 (hypochlorous acid treatment agent) had high reactivity with each impregnation target as compared with chlorine-based treatment agent 1 (chlorous acid treatment agent) (FIG. 1 (b) to FIG. 7 (b), FIG. 8, and FIG. 9). Particularly, when the target was raw stock 1 (rayon), nonwoven fabric 1 (rayon), nonwoven fabric 2 (lyocell), and binder resin 1, chlorine-based treatment agent 2 (hypochlorous acid treatment agent) had high reactivity with the impregnation target (FIG. 1 (b), FIG. 4 (b), FIG. 5 (b), and FIG. 7 (b)). Moreover, it was found that the pH of chlorine-based treatment agent 2 (hypochlorous acid treatment agent) was decreased greatly with passage of time (FIG. 1 (b), FIG. 2 (b), and FIG. 3 (b)).

As understood from the results shown in Table 2, chlorine-based treatment agent 1 (chlorous acid treatment agent) exhibited antimicrobial activity irrespective of whether or not polypeptone, which was the pseudo contaminant, had been added, whereas chlorine-based treatment agent 2 (hypochlorous acid treatment agent) exhibited antimicrobial activity when polypeptone was not added but did not exhibit sufficient antimicrobial activity when polypeptone was added. Alcohol-based disinfectant 1 did not exhibit antimicrobial activity irrespective of whether or not polypeptone was added.

As understood from the results shown in Table 3, the wet wiper including chlorine-based treatment agent 1 (chlorous acid treatment agent) had a higher pseudo contaminant removal ratio than that of the wet wiper including the distilled water. On the other hand, the wet wiper including chlorine-based treatment agent 2 (hypochlorous acid treatment agent) had a pseudo contaminant removal ratio comparable to that of the wet wiper including the distilled water. It should be noted that the wet wiper including alcohol-based disinfectant 1 had a lower pseudo contaminant removal ratio than that of the wet wiper including the distilled water. This is presumably because ethanol decreases a degree of dissolving a protein in water.

The invention claimed is:

1. A wet wiper comprising:
a fabric; and
a chlorine-based treatment agent included in the fabric, wherein, based on a total fiber weight, the fabric comprises 80 wt. % or more of at least one fiber selected from the group consisting of a synthetic fiber, a semi-synthetic fiber, a regenerated fiber, and an inorganic fiber, and
wherein the chlorine-based treatment agent comprises at least one selected from the group consisting of chlorous acid ($HClO_2$) and chlorite ion ($ClO_2^-$), as an effective chlorine component.

2. The wet wiper of claim 1, wherein the wet wiper is accommodated in a package.

3. The wet wiper of claim 1, wherein the fabric comprises the regenerated fiber.

4. The wet wiper of claim 3, wherein the regenerated fiber is rayon, lyocell, or a combination thereof.

5. The wet wiper of claim 1, wherein the fabric is a nonwoven fabric.

6. The wet wiper of claim 5, wherein the nonwoven fabric is a short fiber nonwoven fabric having a fiber length in a range of from 18 to 110 mm.

7. The wet wiper of claim 5, wherein the nonwoven fabric has a weight in a range of from 20 to 200 g/m² and has a thickness in a range of from 0.2 to 1.5 mm.

8. The wet wiper of claim 1, wherein the fabric is a colored fabric.

9. The wet wiper of claim 1, wherein the fabric comprises at least one binder resin selected from the group consisting of polyurethane, acrylic, polyethylene, polyolefin, a petroleum resin, asphalt, an isoprene-based hydrocarbon, a butadiene rubber, and vinyl chloride.

10. The wet wiper of claim 9, wherein the binder resin is a water-emulsifiable polymer.

11. The wet wiper of claim 1, wherein a content of the effective chlorine component in the chlorine-based treatment agent is in a range of from 50 ppm to 1,000 ppm.

12. The wet wiper of claim 7, wherein the weight of the nonwoven fabric is in a range of from 30 to 150 g/m².

13. The wet wiper of claim 7, wherein the thickness of the nonwoven fabric is in a range of from 0.2 to 1.0 mm.

14. The wet wiper of claim 1, wherein, based on the total fiber weight, the fabric comprises 100 wt. % of the at least one fiber synthetic fiber, a semi-synthetic fiber, a regenerated fiber, and an inorganic fiber.

15. The wet wiper of claim 1, wherein the at least one fiber is rayon, lyocell, and/or polyethylene terephthalate.

16. The wet wiper of claim 1, wherein the synthetic fiber is present and is at least one selected from the group consisting of a polyester fiber, an acrylic fiber, a polyolefin fiber, a polyamide fiber, a polyvinyl alcohol fiber, a polyurethane fiber, and a mixture of two or more of any of these.

17. The wet wiper of claim 1, wherein the semi-synthetic fiber is present and is at least one selected from the group consisting of an acetate fiber, a triacetate fiber, and a mixture of two or more of these.

18. The wet wiper of claim 1, wherein the regenerated fiber is present and is at least one selected from the group consisting of a rayon fiber, a lyocell fiber, a cupra fiber, a modal fiber, and a mixture of two or more of these.

19. The wet wiper of claim 1, wherein the inorganic fiber is present and is at least one selected from the group consisting of a glass fiber, a carbon fiber, and a mixture of two or more of any of these.

20. The wet wiper of claim 1, which exhibits antimicrobial activity without the addition of polypeptone.

* * * * *